(12) United States Patent
Brader et al.

(10) Patent No.: US 10,391,062 B2
(45) Date of Patent: Aug. 27, 2019

(54) DRY TRANSGLUTAMINASE COMPOSITION

(75) Inventors: Mark Brader, Virum (DK); Thomas Falck, Brønshøj (DK); Gunhild Klarskov Kristiansen, Bagsværd (DK)

(73) Assignee: Novo Nordisk Healthcare AG, Zurich (CH)

( * ) Notice: Subject to any disclaimer, the term of this patent is extended or adjusted under 35 U.S.C. 154(b) by 421 days.

(21) Appl. No.: 12/937,884

(22) PCT Filed: Apr. 20, 2009

(86) PCT No.: PCT/EP2009/054657
§ 371 (c)(1),
(2), (4) Date: Mar. 10, 2011

(87) PCT Pub. No.: WO2009/130181
PCT Pub. Date: Oct. 29, 2009

(65) Prior Publication Data
US 2011/0165140 A1    Jul. 7, 2011

Related U.S. Application Data

(60) Provisional application No. 61/049,014, filed on Apr. 30, 2008.

(30) Foreign Application Priority Data

Apr. 21, 2008 (EP) ..................... 08103642

(51) Int. Cl.
*A61K 38/45* (2006.01)
*A61K 9/19* (2006.01)
*A61K 38/00* (2006.01)

(52) U.S. Cl.
CPC ............... *A61K 9/19* (2013.01); *A61K 38/00* (2013.01)

(58) Field of Classification Search
CPC ............. A61K 38/00; A61K 9/19; E02D 5/64
See application file for complete search history.

(56) References Cited

U.S. PATENT DOCUMENTS

| | | | | |
|---|---|---|---|---|
| 4,297,344 A | * | 10/1981 | Schwinn | C07K 14/75 514/822 |
| 4,327,086 A | | 4/1982 | Fukushima et al. | |
| 4,877,608 A | | 10/1989 | Lee et al. | |
| 5,164,373 A | | 11/1992 | Shikano et al. | |
| 5,518,742 A | | 5/1996 | Soeda et al. | |
| 5,605,887 A | | 2/1997 | Pines et al. | |
| 5,610,147 A | | 3/1997 | Seelich | |
| 5,612,456 A | * | 3/1997 | Bishop | C12N 9/1044 530/381 |
| 5,691,312 A | | 11/1997 | Paques | |
| 6,204,036 B1 | | 3/2001 | Metzner et al. | |
| 6,447,774 B1 | | 9/2002 | Metzner et al. | |
| 6,593,296 B1 | | 7/2003 | McNamara et al. | |
| 2008/0176789 A1 | * | 7/2008 | Bang | C07K 14/755 514/14.2 |
| 2009/0311240 A1 | * | 12/2009 | Mittermayr et al. | 424/94.64 |

FOREIGN PATENT DOCUMENTS

| | | |
|---|---|---|
| CN | 1214633 A | 4/1999 |
| EP | 430200 | 11/1989 |
| EP | 499679 | 8/1992 |
| EP | 637451 | 8/1993 |
| EP | 0754463 A2 | 1/1997 |
| EP | 1131110 A1 | 9/2001 |
| JP | 2-204407 A | 8/1990 |
| JP | 4-207194 A | 7/1992 |
| JP | 6-284867 A | 10/1994 |
| JP | 2001-149045 A | 6/2001 |
| JP | 2003/055257 | 2/2003 |
| JP | 2004-123566 A | 4/2004 |
| JP | 2006505508 A | 2/2006 |
| JP | 2007182434 A | 7/2007 |
| KR | 20020092469 A | 12/2002 |
| RU | 2314825 C2 | 1/2008 |
| WO | 9422470 A1 | 10/1994 |
| WO | 9640780 A1 | 12/1996 |
| WO | 0029041 A1 | 5/2000 |
| WO | 01/85198 | 11/2001 |
| WO | 02/36155 A1 | 5/2002 |
| WO | 2004007533 A1 | 1/2004 |

OTHER PUBLICATIONS

Huang et al., Shipin Yu Fajiao Gongye, "Inhibition of the Protease in the Preparation of Microbial Transglutaminase", 2005, vol. 31, No. 12, pp. 8-112.
Cui et al., Process Biochemistry, 2006, vol. 41, No. 6, pp. 1427-1431.
Database CA (Online), Chemical Abstracts Service, Columbus, Ohio, US, 2007, XP002578620.
Database CA (Online), Chemical Abstracts Service, Columbus, Ohio, US, 1990, XP002578619.
Dong et al., Spectroscopic study of secondary structure and thermal denaturation of recombinant human factor XIII, Arch. Biochem. Biophys. (1997), 347, 213-220.
Kreilgaard et al., Effect of tween 20 on freeze-thawing and agitation-induced aggregation of recombinant human factor XIII, J. Pharm. Sci. 87, 1998, 1597-1602.
Kreilgaard et al., Effects of additives on the stability of recombinant human factor XIII during freezedrying and storage in the dried solid, Arch. Biochem. Biophys. 360, 1998, 121-134.

(Continued)

*Primary Examiner* — Lisa J Hobbs
(74) *Attorney, Agent, or Firm* — Leon Y. Lum (57) ABSTRACT

The present invention relates to a dry transglutaminase composition, said composition is obtainable by lyophilizing or spray-drying an aqueous composition comprising a transglutaminase, a salt and at least one further component selected from the group consisting of a sugar, an amino acid, and a buffer, wherein the concentration of the salt in the aqueous composition is in the range from 5 to 100 mM. In further aspects, the present invention relates to a method of preparing said dry transglutaminase composition, a reconstituted solution, a pharmaceutical composition, and method of treatments.

26 Claims, 2 Drawing Sheets

(56) References Cited

OTHER PUBLICATIONS

Turner et al., Mapping of factor XIII solvent accessibility as a function of activation state using chemical modification methods, Bio. Chem., 43, 2004, 9755-9765.
Polgar et al., Non-proteolytic activation of cellular protransglutaminase (placenta macrophage factor XIII), Biochem. J., 267, 1990, 557-560.
Carpenter et al., Rational design of stable lyophilized protein formulations: Some practical advice, Pharm. Research, 14, 1997, 969-975.
Wang Wei, Lyophilization and development of solid protein pharmaceuticals, International Journal of Pharmaceutics, vol. 203, Issues 1-2, 2000, pp. 1-60.
Formulation design studies of rFXIII drug product, MrkB (2007) Internal technical report to be filed in Novodocs, pp. 1-74.
Carpenter J F et al: Rational Design of Stable Lyophilized Protein Formulations: Theory and Practice, Journal :Pharmaceutical Biotechnology, Kluwer, Dordrecht, NL, vol. 13, Year: Jan. 1, 2002 (Jan. 1, 2002), pp. 109-133.
Zhang Q. et al (Editors in chief)., Pharmaceutics, Peking University Medical Press, 2005, p. 123.

\* cited by examiner

Evaluation of sucrose and NaCl levels. Modde analysis of effect of 25mM NaCl on AIE-HPLC purity of samples stored at 40°C.

FIG. 1

Full factorial study of NaCl and histidine levels. Modde analysis of 25°C rFXIIIa° data.

FIG. 2

Full factorial study of NaCl and histidine levels. Modde analysis of AIE-HPLC purity data.

DRY TRANSGLUTAMINASE COMPOSITION

CROSS-REFERENCE TO RELATED APPLICATIONS

This application is a 35 U.S.C. § 371 national stage application of International Patent Application PCT/EP2009/054657 (published as WO 2009/130181 A2), filed Apr. 20, 2009, which claimed priority of European Patent Application 08103642.8, filed Apr. 21, 2008; this application further claims priority under 35 U.S.C. § 119 of U.S. Provisional Application 61/049,014, filed Apr. 30, 2008.

FIELD OF THE INVENTION

The present invention relates to transglutaminase compositions, in particular stable lyophilized or spray-dried compositions of blood coagulation Factor XIII, and furthermore it concerns methods of preparing said compositions, reconstituted solutions, pharmaceutical compositions, and method of treatments.

BACKGROUND OF THE INVENTION

Transglutaminases are $Ca^{2+}$ dependent enzymes that catalyze the formation of isopeptide bonds in proteins between the side chain γ-carboxamide group of glutamine and the side chain ε-amino group of lysine. Transglutaminases are found both extracellularly and intracellularly. Examples of transglutaminases include Factor XIII, epidermal transglutaminases, type II transglutaminases (tissue type transglutaminase, liver transglutaminases), and type I transglutaminases (keratinocyte transglutaminase).

Blood coagulation Factor XIII (FXIII) is a plasma transglutaminase also known as "fibrinoligase" and "fibrin stabilizing factor" it circulates in plasma in a concentration of 20 microgram/ml. This protein exists in plasma as a tetramer comprised of two A subunits and two B subunits ($A_2B_2$). Each subunit has a molecular weight of approximately 80 000 Da, and the complete protein has a molecular weight of approximately 330 000 Da. The A subunits contain the transglutaminase catalytic site, whereas the B subunits have no catalytic activity but acts as a structural protein protecting the A subunits from clearance.

Factor XIII is dependent on thrombin and $Ca^{2+}$ for activation. Thrombin cleaves on the C-terminal side of Arg37 in the A subunits, thereby releasing the activation peptide (residues 1-37 of the A subunit) and the B subunits and leaving the active form of the $A_2$ dimer. The activated FXIII $A_2$ subunit (FXIIIa) is the catalytically active form of FXIII.

The FXIII enzyme is the last enzyme to be activated in the coagulation cascade and functions to cross-link α- and γ-fibrin chains, resulting in a stronger clot with an increased resistance to fibrinolysis. Furthermore a number of antifibrinolytic, pro-haemostatic and adhesive proteins are cross-linked to the clot thereby providing a strong fibrin structure with increased mechanical resistance to the dissolution by plasmin and other proteolytic enzymes.

Commercially available purified or partially purified transglutaminase or Factor XIII preparations, in many cases, contain added stabilizers, such as human serum albumin (HSA). The use of protein stabilizers is problematic, since it decreases protein specific activity, increases the protein load when administered to patients, and may interfere with assessment of purity. It may also make the protein preparation immunogenic. These disadvantages of protein stabilizers make them particularly disadvantageous for stabilizing highly purified proteins, such as recombinant proteins. Additionally, use of protein stabilizers causes potential contamination with viral antigens when albumin, for example, is added.

FXIII, isolated from placenta or plasma or in the form of fresh frozen plasma, has been employed for many years for treatment of Factor XIII deficiency. These formulations, however, suffer from disadvantages of containing foreign proteins, with all the problems attached thereto such as unwanted immunogenicity.

It is now possible to prepare transglutaminases and Factor XIII using recombinant DNA technology. As used herein, rFXIII refers to recombinant Factor XIII. However, up to date there is no commercially available rFXIII product on the market.

The composition and activity of protein preparations used in therapy must be stable over relatively long periods of time. It is only rarely possible to achieve this stability in solution and, therefore, such products are frequently marketed in the dry state. Mild freeze-drying (lyophilization) is one of the methods of choice for drying such products. However, even when this method is used, stable preparations fulfilling the requirements for integrity and durability are difficult to achieve.

Freeze-drying of transglutaminase or Factor XIII solutions may for instance, for example, lead to a marked drop in activity and lose of purity. A further problem for freeze-drying of, for example, Factor XIII is created by a degradation product of Factor XIII the so called non-proteolytically activated species) ($FXIIIa^0$), also referred to as pre-activated Factor XIII. $FXIIIa^0$ is believed to pose a severe toxicity risk and injection of this may cause potentially undesirable side effects. It is therefore desirable to stabilize transglutaminase or Factor XIII formulations against formation of non-proteolytically activated products.

Various dry FXIII compositions are known in the prior art. Below are disclosed examples of disclosures of lyophilized FXIII compositions. WO2002/36155 describes that a lyophilized FXIII composition may be formulated with 1 mM EDTA, 10 mM Glycine, 2% sucrose in water, or with 20 mM Histidine, 3% wt/vol sucrose, 2 mM Glycine, and 0.01% wt/vol polysorbate, pH 8.0. U.S. Pat. No. 6,204,036 (Aventis Behring) concerns a stable lyophilized transglutaminase formulation comprising at least one additive selected from the group of D- and L-amino acids and salts, derivatives, homologs and dimers thereof, sugars and sugar alcohols, surface active ingredients, and reducing agents with the proviso that the additive is not glycine nor arginine, wherein the formulation does not contain a protein stabilizer and wherein said formulation is soluble without any turbidity in an aqueous solvent suitable for parenteral administration.

These formulations mentioned above, however may suffer from the disadvantage, described above, of high levels of non-proteolytically activated Factor XIII, which is considered an obstacle for clinical and commercial feasibility of these formulations. It is apparent, therefore, that stable dry transglutaminase and Factor XIII formulations with low levels of non-proteolytically activated products are greatly desired. Furthermore, such formulations should not require the addition of protein stabilizers, for example HSA.

SUMMARY OF THE INVENTION

The present invention is based on the surprising discovery that salts, e.g. monovalent salts, confers a significant stabilizing effect to dry transglutaminase, e.g. Factor XIII, compositions with respect to purity and to the formation of pre-activated transglutaminases. This effect is shown to be specific to the dry state and has particular significance for producing a stable commercial product.

In one aspect, the present invention provides a dry transglutaminase composition, said composition is obtainable by lyophilizing or spray-drying an aqueous composition comprising a transglutaminase, a salt and at least one further component selected from the group consisting of a sugar, an amino acid, and a buffer, wherein the concentration of the salt in the aqueous composition is in the range from 5 to 100 mM.

In further aspects, the present invention provides a method of preparing said dry transglutaminase composition, a reconstituted solution, a pharmaceutical composition, and a method of treatment.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DEFINITIONS

The terms "pre-activated" or "non-proteolytically activated" transglutaminase, in relation to the present invention, refers to a transglutaminase that has been non-proteolytically activated, for example when Factor XIII becomes activated without the presence of thrombin (thrombin has the ability to proteolytically cleave FXIII), it is said to be non-proteolytically activated; for references see, for example, Polgar J., et al. *Biochem J* 1990; 267: 557-60. Muszbek L., et al. *Thrombosis Research* 94 (1999) 271-305. Non-proteolytically activated Factor XIII) (FXIII°), which is a degradation product of FXIII, is threatening to the viability of a pharmaceutical FXIII composition because this degradation product is believed to pose a severe toxicity risk.

The term "biologically active" as used herein means having activity in a living being, such as a medical, agricultural or cosmetic activity.

The term "aqueous composition", in relation to the present invention, refers to a composition comprising liquid water. Such a composition is typically a solution or a suspension. The term "aqueous composition" as employed in the context of the present invention refers to a formulation comprising at least 50% by weight (w/w) of water.

The term "diluent", in relation to the present invention, refers to a liquid solution or suspension. The term "diluent" as employed in the context of the present invention refers to a solution or a suspension comprising at least 50% by weight (w/w) of water. In context of the present invention the diluent is used in the reconstitution of the dry transglutaminase composition.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

DESCRIPTION OF THE INVENTION

The present invention provides transglutaminase compositions, in particular stable lyophilized or spray-dried compositions of transglutaminases, e.g. blood coagulation Factor XIII (FXIII). The invention also provides methods of preparing said dry transglutaminase compositions, reconstituted solutions, pharmaceutical compositions, and method of treatments.

The present invention provides a product comprising a transglutaminase, e.g. a Factor XIII, with a level of purity and a level of pre-activation, that remains acceptable throughout the manufacturing process, storage and in-use period of the transglutaminase product.

The compositions of the present invention, which provides improved stability in respect to the level of pre-activation and in respect to total purity, comprises a dry transglutaminase composition, said composition is obtainable by lyophilizing or spray-drying an aqueous composition comprising a transglutaminase, a salt and at least one further component selected from the group consisting of a sugar, an amino acid, and a buffer, wherein the concentration of the salt in the aqueous composition is in the range from 5 to 100 mM.

In one embodiment, the dry composition of the present invention comprises a dry transglutaminase composition, said composition is obtainable by lyophilizing or spray-drying an aqueous composition comprising a transglutaminase, a salt and at least one further component selected from the group consisting of a sugar, an amino acid, and a buffer, wherein the concentration of the salt in the aqueous composition is in the range from 5 to 100 mM, with the proviso that the composition is not a dry Factor XIII composition obtained by lyophilizing a Factor XIII solution containing 0.5% NaCl and 2.25% glycine.

In one embodiment, the dry composition of the present invention does not contain any protein stabilizers, such as albumin.

The embodiments and examples described below mainly describe and disclose compositions of recombinant FXIII (rFXIII), but the present invention is not limited to these embodiments and examples, but may be applied to compositions of any transglutaminase presently known or that is discovered in the future.

Components of the Composition

The composition of the present invention comprises a transglutaminase. Examples of transglutaminases that could be stabilized by the formulation of the present invention include, but are not limited to, Factor XIII, epidermal transglutaminases, type II transglutaminases (tissue type transglutaminase, liver transglutaminases), and type I transglutaminases (keratinocyte transglutaminase).

Factor XIII

In one embodiment, the aqueous composition to be lyophilized or spray-dried comprises a Factor XIII compound. The Factor XIII compound may for instance be a naturally occurring wild-type Factor XIII and naturally occurring allelic variants of Factor XIII. These FXIII compounds may for instance originate from human or other animal sources, e.g. human FXIII, porcine FXIII and bovine FXIII. The wild-type sequence of human Factor XIII may for instance be found in EP 268772 and EP 236978. The Factor XIII compound, of the present invention, include the complete Factor XIII zymogen tetramer ($A_2B_2$) and Factor XIIIa, as well as subunits thereof, including the A subunit and $A_2$ dimers.

The Factor XIII compound, of the present invention, may for instance be biologically active fragments, derivatives or variants of Factor XIII that retain at least part of the characteristic cross-linking activity of the wild-type Factor XIII. This cross-linking activity may be measured by methods known in the art.

In some embodiments, the biologically active fragments, derivatives or variants of Factor XIII retain 10%, 20%, 30%, 40%, 50%, 60%, 70%, 80%, 90%, or 100% of the cross-linking activity of the wild-type Factor XIII.

Fragments, derivatives, and variants of Factor XIII include substitutional, insertional and deletional variants. Insertional variants comprise amino and/or carboxyl terminal fusions as well as intrasequence insertions of single or multiple amino acid residues. Insertions may for instance be introduced within the mature coding sequence of the wild-type Factor XIII protein. Deletion variants are characterized by the removal of one or more amino acid residues from the wild-type Factor XIII protein. These variants ordinarily are prepared by site specific mutagenesis of nucleotides in the DNA encoding the protein, thereby producing DNA encoding the variant, and thereafter expressing the DNA in recombinant cell culture. However, variant protein fragments may also be prepared by in vitro synthesis. While the site for introducing an amino acid sequence variation ordinarily is predetermined, the mutation itself need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence are well known, for example, M13 primer mutagenesis. Substitutional variants are those where at least one residue sequence has been removed and a different residue inserted in its place. Amino acid substitutions are typically of single residues; insertions usually will be in order of about from 1 to 10 amino acid residues; and deletions will range from about 1 to 30 residues. Deletions or insertions may for instance be made in adjacent pairs, i.e., a deletion of 2 residues or insertion of 2 residues. Substitutions, deletions, insertions or any combination thereof may be combined to arrive at a final construct. Obviously, the mutations that will be made in the DNA encoding the variant protein must not place the sequence out of reading frame and preferably will not create complementary regions that could produce secondary mRNA structure. An example of a genetically engineered variant of Factor XIII is the Val34Leu variant of wild-type human Factor XIII (i.e. a variant in which the Val residue at position 34 in the amino acid sequence of wild-type human Factor XIII is replaced by a leucine residue).

The Factor XIII, of the present invention, may be purified from a wide variety of biological materials, including lysates, homogenizates or extracts of cells which naturally produce a Factor XIII, but also of cells which have been genetically modified to produce a Factor XIII, such as yeast cells transformed with DNA coding for a Factor XIII. An example of a method of purifying Factor XIII is disclosed in WO/2006/021584.

The Factor XIII, of the present invention, may for instance be prepared by recombinant DNA technology. Methods for preparing recombinant Factor XIII are known in the art. See, for example, Davie et al., EP 268.772; Grundmann et al., AU-A-69896/87; Bishop et al., Biochemistry 1990, 29: 1861-1869; Board et al., Thromb. Haemost. 1990, 63: 235-240; Jagadeeswaran et al., Gene 1990, 86: 279-283; and Bröker et al., FEBS Lett. 1989, 248: 105-110. Within one embodiment, the Factor XIII $A_2$ dimer is prepared cytoplasmically in the yeast *Saccharomyces cerevisiae* as disclosed in U.S. patent application Ser. No. 07/741,263. The cells are harvested and lysed, and a cleared lysate is prepared. The lysate is fractionated by anion exchange chromatography at neutral to slightly alkaline pH using a column of derivatized agarose, such as DEAE Fast-Flow Sepharose™ (Pharmacia) or the like. Factor XIII is then precipitated from the column eluate by concentrating the eluate and adjusting the pH to 5.2-5.5, such as by diafiltration against ammonium succinate buffer. The precipitate is then dissolved and further purified using conventional chromatographic techniques, such as gel filtration and hydrophobic interaction chromatography.

In one embodiment of the present invention, the Factor XIII is a recombinant Factor XIII. In one embodiment of the present invention, the Factor XIII is human Factor XIII. In one embodiment of the present invention, the Factor XIII is recombinant human Factor XIII. In one embodiment of the present invention, the Factor XIII is a dimer of A subunits.

The concentration of Factor XIII, in the aqueous composition to be lyophilized or spray-dried, may for instance be varied in a wide range, and is in one embodiment in the range of 0.003-100 mg/ml, in a further embodiment in the range of 1-30 mg/ml, and in a still further embodiment in the range of 2-15 mg/ml.

Salts

The aqueous composition of the invention comprises a salt or mixtures of salts. The salt is used to improve the stability of the dry composition in respect to pre-activation and in respect to total purity. The diluent of the invention may for instance comprise a salt or mixtures of salts. In some embodiments the salt is a monovalent salt. Examples of monovalent salts that may for instance be used include, but are not limited to, sodium chloride, potassium chloride, sodium acetate, sodium sulphate, sodium gluconate and mixtures thereof. In some embodiments the salt is a divalent salt. In some embodiments the salt is a divalent salt with the proviso that the divalent salt is not a Ca (II) salt.

The concentration of the salt, e.g. NaCl, employed may for instance be varied within a certain range, and is in one embodiment in the range of 5-100 mM, in further embodiments in the ranges of 5-99 mM, 7-95 mM, 8-90 mM, 10-80 mM, 15-70 mM, 25-75 mM, and 20-60 mM and in a still further embodiment in the range of 25-50 mM.

Sugar and Sugar Alcohols

In some embodiments of the present invention, the aqueous composition to be lyophilized or spray-dried comprises one or more sugars or sugar alcohols. The diluent used for reconstitution of the dried composition may for instance comprise one or more sugars or sugar alcohols. Sugars or sugar alcohols may be used to stabilize proteins in the dry composition of the invention during freeze drying by preventing physical/chemical destabilizing effects (e.g. unfolding). Examples of sugars or sugar alcohols that may for instance be used include, but are not limited to sucrose, mannitol, trehalose, lactose, maltose, sorbitol, raffinose, dextrins, cyclodextrins, and the derivatives, homologs, and mixtures thereof.

The concentration of sugar and sugar alcohol employed may for instance be varied in a wide range, and is in one embodiment in the range of 0.1-15% (w/w), in a further embodiment in the range of 0.1-8.5% (w/w), and in a still further embodiment in the range of 0.5-5.0% (w/w).

Amino Acids

In some embodiments of the present invention, the aqueous composition to be lyophilized or spray-dried comprises one or more amino acids. In some embodiments of the present invention, the diluent used for reconstitution of the dried composition may comprise one or more amino acids. Amino acids may for instance be used to improve stability of the lyophilized or spray-dried composition. In one embodiment, the one or more amino acids are used to decrease aggregate formation of the transglutaminase, e.g. the FXIII, during storage of the composition. Examples of amino acids that may be used include, but are not limited to glycine, histidine, arginine, glutamic acid, methionine, threonine, lysine, alanine, isoleucine, and cysteine (Gly, His, Arg, Glu, Met, Thr, Lys, Ala, Ile, and Cys) and the salts, derivatives, homologs, dimers, oligomers, and mixtures thereof.

Suitable derivatives and homologs are well known. Suitable derivatives include, but are not limited to: esters, thioesters, and amides of the carboxyl group; acylated derivatives of the amino group, including urethane derivatives; and esters, amides, and esters of side-chain functional groups. Suitable homologs include, for example, ornithine (homolog of lysine), homoserine, and α-aminobutyric acid. Physiologically acceptable salts are also well known in the art and are described in, for example, Remington's Pharmaceutical Science: Drug Receptors and Receptor Theory, (18th ed.), Mack Publishing Co., Easton Pa. (1990).

The concentrations of the amino acids employed may for instance be in the range of 0.01-10% (w/w), or in the range of 0.1-3% (w/w).

Buffers

In some embodiments of the present invention, the aqueous composition to be lyophilized or spray-dried, and/or the diluent used for reconstitution of the dried composition comprises a buffer. A buffer is a solution comprising a substance, which substance is capable of preventing significant changes in the pH of solutions to which small amounts of acids or bases are added and thereby of maintaining largely the original acidity or basicity of the solution. A buffer usually comprises a weak acid or weak base together with a salt thereof.

The pH of the aqueous compositions could be in the range from 2 to 10, particularly between 7 and 8. The amino acids described above or buffers, having a pH in the range of 2 to 10 could be used for effecting the buffering. Examples of buffers that may for instance be used include, but are not limited to, acetate buffers, carbonate buffers, citrate buffers, glycylglycine buffers, histidine buffers, glycine buffers, lysine buffers, arginine buffers, phosphate buffers (containing, e.g. sodium dihydrogen phosphate, disodium hydrogen phosphate or trisodium phosphate), TRIS [tris(hydroxymethyl)aminomethane] buffers, bicine buffers, tricine buffers, malate buffers, succinate buffers, maleate buffers, fumarate buffers, tartrate buffers, aspartate buffers, and mixtures thereof. In some embodiments, citrate buffers, histidine buffers, sodium phosphate buffers, succinate buffers, and TRIS buffers, are used. In one embodiment, histidine is used.

The concentrations of the buffer employed may for instance be in the range 0-50 mM, or in the range of 0-25 mM.

Other Components

One or more other components may also be incorporated in the aqueous composition to be lyophilized or spray-dried, and/or the diluent used for reconstitution of the dried composition. Such additional ingredients include, but are not limited to, non-ionic surfactants, reducing agents, chelating agents, antioxidants, preservatives, wetting agents, emulsifiers, bulking agents, tonicity modifiers (tonicity-adjusting agents), oleaginous vehicles, proteins (e.g. human serum albumin, gelatin or other proteins) and zwitterionic substances (e.g. betaine, taurine or an amino acid such as arginine, glycine, lysine or histidine). Such additional ingredients should not, of course, adversely affect the overall stability of the aqueous composition or the dry composition of the present invention. In this respect, reference is made to Remington: The Science and Practice of Pharmacy, 19th edition, 1995.

Non-Ionic Surfactants

In some embodiments of the present invention, the aqueous composition to be lyophilized or spray-dried, and/or the diluent used for reconstitution of the dried composition comprises a non-ionic surfactant. Ionic surfactants are surface active agents which exert their effect by shielding proteins from critical surfaces (e.g. packaging, solids) Ionic surfactants may for instance be used to improve stability of the lyophilized or spray-dried composition. Examples of non-ionic surfactants that may for instance be used include, but are not limited to, Tween 80, Tween 20, PEG, acetyl alcohol, PVP, PVA, lanolin alcohol, sorbitan monooleate, poloxamers, and polyoxyethylene alkyl ethers. In one embodiment, Tween 20 is used.

The concentrations of the non-ionic surfactant employed may for instance be in the range of 0.00001-5% (w/w), or in the range of 0.0002% and 0.1% (w/w).

Reducing Agents

In some embodiments of the present invention, the aqueous composition to be lyophilized or spray-dried, and/or the diluent used for reconstitution of the dried composition comprises a reducing agent. Reducing agents, such as antioxidants, are used for removing free radicals that could destabilize proteins. Examples of reducing agents that may for instance be used include, but are not limited to, cysteine, N-acetyl-cysteine, thioglycerol, sodium sulphide, tocopherols, and glutathione.

Chelating Agents

In some embodiments of the present invention, the aqueous composition to be lyophilized or spray-dried, and/or the diluent used for reconstitution of the dried composition comprises a chelating agent. Chelating agents are used to remove metals (iron, copper) from the formulation and usually tend to protect proteins from metal-catalyzed reactions. Examples of chelating agents that may for instance be used include, but are not limited to, salts of EDTA, citric acid and aspartic acid, and mixtures thereof. In one embodiment of the present invention, the chelating agent is present in a concentration from 0.1 mg/ml to 5 mg/ml. In one embodiment of the present invention the chelating agent is present in a concentration from 0.1 mg/ml to 2 mg/ml. In a further embodiment of the present invention the chelating agent is present in a concentration from 2 mg/ml to 5 mg/ml.

Antioxidants

In some embodiments of the present invention, the aqueous composition to be lyophilized or spray-dried, and/or the diluent used for reconstitution of the dried composition comprises an antioxidant. In one embodiment, the aqueous composition comprises methionine (or another sulphur-containing amino acid or amino acid analogue) to inhibit oxidation of methionine residues to their sulfoxide form when the transglutaminase, e.g. the FXIII, is a polypeptide comprising at least one methionine residue susceptible to such oxidation. The term "inhibit oxidation" is intended to indicate minimization of accumulation of oxidized species (of methionine) with time. Inhibition of methionine oxidation results in greater retention of the polypeptide in its proper molecular form. Any stereoisomer of methionine (L, D or DL isomer) or combinations thereof may for instance be used. The amount to be added should be an amount sufficient to inhibit oxidation of the methionine residues such that the amount of sulfoxide form of methionine is acceptable to regulatory agencies. Typically, this means that the composition contains no more than from about 10% to about 30% methionine sulfoxide form. This may for instance in general be achieved by adding methionine in an amount such that the molar ratio of added methionine to methionine residues ranges from about 1:1 to about 1000:1, such as 10:1 to about 100:1.

Preservatives

In some embodiments of the present invention, the aqueous composition to be lyophilized or spray-dried, and/or the diluent used for reconstitution of the dried composition comprises a preservative. Preservatives may be added for regulatory requirements to multiple dosage containers. Preservatives are used as anti-microbial agent to protect from microbial contamination during multiple dosage withdrawal from vials. Examples of preservatives that may for instance be used include, but are not limited to, phenol, o-cresol, m-cresol, p-cresol, chlorocresol, methyl p-hydroxybenzoate, ethyl p-hydroxybenzoate, propyl p-hydroxybenzoate, butyl p-hydroxybenzoate, 2-phenoxyethanol, 2-phenylethanol, benzyl alcohol, chlorobutanol, thimerosal, bronopol, benzoic acid, imidurea, chlorohexidine, sodium dehydroacetate, benzethonium chloride, chlorphenesine (3-p-chlorophenoxypropane-1,2-diol) and mixtures thereof. The preservative may for instance be present in a concentration from 0.1 mg/ml to 20 mg/ml. In one embodiment of the present invention the preservative is present in a concentration from 0.1 mg/ml to 5 mg/ml. In a further embodiment of the present invention the preservative is present in a concentration from 5 mg/ml to 10 mg/ml. In another embodiment of the present invention the preservative is present in a concentration from 10 mg/ml to 20 mg/ml.

One skilled in the art would be able to use the methods described below to analyze the effects on stability, pre-activation and purity of the one or more added components in the dry composition or aqueous composition, of the invention, with only routine experimentation.

Dry Composition—Powder

After lyophilization or spray-drying the composition of the invention will be in a dry form. The dry composition of the invention may for instance be solid, powder or granular material. In one embodiment, the dry composition of the invention is a powder. The level of residual moisture in this dried composition is important for the stability of the dry transglutaminase, e.g. FXIII, during storage. In one embodiment of the invention, the dry composition contains less than 3% residual moisture. In a further embodiment, the dry composition contains less than 1% residual moisture.

Drying Techniques and Reconstitution

Lyophilization and spray-drying of the aqueous composition of the present invention may be performed by using methods of lyophilization and spray-drying well known to those of skill in the art: for lyophilization see, for example, Williams and Polli (1984), *J. Parenteral Sci. Technol.* 38:48-59. for spray-drying see, for example, Masters in Spray-Drying Handbook (5th ed; Longman Scientific and Technical, Essex, U.K., 1991), pp. 491-676; Broadhead et al. (1992) *Drug Devel. Ind. Pharm.* 18:1169-1206; and Mumenthaler et al. (1994) *Pharm. Res.* 11:12-20. Other drying techniques may also be used, such as air-drying, see Carpenter and Crowe (1988), *Cryobiology* 25:459-470; and Roser (1991) Biopharm. 4:47-53.

In relation to the present invention, when reference is made to lyophilization and spray-drying, it is also contemplated that other drying techniques could be used. For example, the expression "aqueous composition to be lyophilized or spray-dried", in relation to the present invention, is also meant to include an "aqueous composition to be dried with other drying techniques".

In one embodiment, the dry composition of the present invention is obtained by lyophilization. The lyophilization process typically includes the following steps: a freezing step, a primary drying step and a secondary drying step. In the freezing step, the aqueous composition is cooled. The temperature and duration of the freezing step is chosen such that all of the components in the composition are completely frozen. For example, a suitable freezing temperature is approximately −40° C. In the primary drying step, the ice formed during freezing is removed by sublimation at sub-ambient temperatures under vacuum. For example, the chamber pressure used for sublimation may for instance be from about 40 mTorr to 400 mTorr, and the temperature may for instance be between −30° C. to −5° C. After primary drying, any residual amounts of liquid which could not be removed by sublimation is removed by secondary drying, i.e., desorption. The temperature during secondary drying is near or greater than ambient temperature.

In one embodiment of the invention, an annealing (heating step) is introduced in the freezing step during lyophilization. This heating is performed to temperatures below the freezing point of the formulation. This annealing (heating step) may further stabilize the dry composition of the invention.

Reconstitution

At a desired stage, for example when it is time to administer the transglutaminase, e.g. the FXIII, to a patient, the dry composition of the invention may be reconstituted with a diluent. Reconstitution generally takes place at a temperature of about 25° C. to ensure complete hydration, although other temperatures may be employed as desired. The time required for reconstitution will depend, e.g. on the type of diluent, and amount of transglutaminase and other components.

In one embodiment of the invention, the diluent is distilled water. It may for instance be an advantage to use distilled water, because a separate, customized diluent does not need to be manufactured.

In one embodiment of the invention, the diluent is ethanol.

In one embodiment of the invention, the diluent may for instance comprises one or more components such as salts, sugars, amino acids, buffers, non-ionic surfactants, reducing agents, chelating agents, antioxidants, preservatives, wetting agents, emulsifiers, bulking agents, tonicity modifiers, oleaginous vehicles, proteins (e.g. human serum albumin, gelatin or other proteins) and zwitterionic substances. Which components to include in the diluent and the amount of these components, is governed by the desired effect to be achieved by these components. Examples of diluents include, but are not limited to, bacteriostatic water for injection (BWFI), a pH buffered solution (e.g. phosphate-buffered saline), a sterile saline solution, and a dextrose solution.

The protein concentration in the reconstituted solution is at least 5 mg/ml, for example from about 10 mg/ml to about 400 mg/ml, from about 20 mg/ml to about 200 mg/ml, or from about 30 mg/ml to about 150 mg/ml. High protein concentrations in the reconstituted solution are considered to be particularly useful where subcutaneous delivery of the reconstituted solution is intended. However, for other routes of administration, such as intravenous administration, lower concentrations of the protein in the reconstituted solution may be desired (for example from about 5-50 mg/ml, or from about 10-40 mg/ml protein in the reconstituted solution). In certain embodiments, the protein concentration in the reconstituted solution is significantly higher than that in the pre-dried formulation. For example, the protein concentration in the reconstituted solution may be about 2-40 times, 3-10 times and or 3-6 times (e.g. at least three fold or at least four fold) that of the pre-dried aqueous composition.

In one embodiment of the present invention, the dry transglutaminase composition, e.g. comprising a Factor XIII, is stable for more than 3 years of storage, and the reconstituted solution is stable for more than 6 weeks of usage. In one embodiment of the present invention, the dry transglutaminase composition, e.g. comprising a Factor XIII, is stable for more than 2 years of storage, and the reconstituted solution is stable for more than 4 weeks of usage. In one embodiment of the present invention, the dry transglutaminase composition, e.g. comprising a Factor XIII, is stable for more than 1 years of storage, and the reconstituted solution is stable for more than 2 weeks of usage. In one embodiment of the present invention, no more than 1% of the reconstituted Factor XIII composition, is non-proteolytically activated Factor XIII. In one embodiment of the present invention, no more than 0.5% of the reconstituted Factor XIII composition, is non-proteolytically activated Factor XIII.

Exemplary Variants

Table 1 and 2 disclose non-limiting list of exemplary variants of the invention.

TABLE 1

A non-limiting list of exemplary variants

| composition | Fill solution concentration | Fill solution solids (mg/ml) | Reconstituted osmolarity (mM) |
|---|---|---|---|
| 5 ml fill; 2.5 ml reconstitution | | | |
| Protein | 2.5 | 0 | 2.5 | 0 |
| Sucrose | 26 mg/ml | 75 | 26 | 150 |
| Histidine | 20 mM | 20 | 3.1 | 40 |
| NaCl | 25 mM | 25 | 1.45 | 100 |
| Polysorbate 20 | 0.01% | 0 | 0 | 0 |
| | | | 33.05 | 290 |
| 6 ml fill; 3 ml reconstitution | | | | |
| Protein | 2.5 | 0 | 2.5 | 0 |
| Sucrose | 26 mg/ml | 75 | 26 | 150 |
| Histidine | 20 mM | 20 | 3.1 | 40 |
| NaCl | 25 mM | 25 | 1.45 | 100 |
| Polysorbate 20 | 0.01% | 0 | 0 | 0 |
| | | | 33.05 | 290 |
| 3 ml Fill reconstitute with 3 ml | | | | |
| Protein | 5.0 mg/ml | 0 | 5 | 0 |
| Sucrose | 55 mg/ml | 160 | 55 | 160 |
| Histidine | 20 mM | 20 | 3.1 | 20 |
| NaCl | 50 mM | 50 | 2.9 | 100 |
| Polysorbate 20 | 0.01% | 0 | 0 | 0 |
| | | | 66 | 280 |
| 3 ml Fill reconstitute with 3 ml | | | | |
| Protein | 5.0 mg/ml | 0 | 5 | 0 |
| Sucrose | 72 mg/ml | 210 | 72 | 210 |
| Histidine | 20 mM | 20 | 3.1 | 20 |
| NaCl | 25 mM | 25 | 1.45 | 50 |
| Polysorbate 20 | 0.01% | 0 | 0 | 0 |
| | | | 81.55 | 280 |
| 3 ml Fill reconstitute with 3 ml | | | | |
| Protein | 5.0 mg/ml | 0 | 5 | 0 |
| Sucrose | 48 mg/ml | 140 | 48 | 140 |
| Histidine | 40 mM | 40 | 6.2 | 40 |
| NaCl | 50 mM | 50 | 2.9 | 100 |
| Polysorbate 20 | 0.01% | 0 | 0 | 0 |
| | | | 62.1 | 280 |
| 4 ml Fill reconstitute with 2 ml | | | | |
| Protein | 5.0 mg/ml | 0 | 5 | 0 |
| Sucrose | 26 mg/ml | 76 | 26 | 152 |
| Histidine | 20 mM | 20 | 3.1 | 40 |
| NaCl | 25 mM | 25 | 1.45 | 100 |
| Polysorbate 20 | 0.01% | 0 | 0 | 0 |
| | | | 35.55 | 292 |
| 2 ml fill; 3 ml reconstitution | | | | |
| Protein | 7.5 | 0 | 7.5 | 0 |
| Sucrose | 85 mg/ml | 250 | 57 | 166 |
| Histidine | 20 mM | 20 | 3.1 | 13 |
| NaCl | 50 mM | 50 | 2.9 | 33 |
| Polysorbate 20 | 0.01% | 0 | 0 | 0 |
| | | | 70.5 | 212 |

TABLE 2 non-limiting exemplary variant
12 ml vial filled with 3 ml filling solution,
lyophilized, then reconstituted with 3 ml water

| Filling solution | Lyophilized vial (powder) | Reconstituted vial |
|---|---|---|
| 5 mg/ml rFXIII | 15 mg | 5 mg/ml |
| 55 mg/ml Sucrose | 165 mg | 55 mg/ml |
| 20 mM Histidine | 9.3 mg | 20 mM |
| 0.01% Polysorbate 20 | 0.3 mg | 0.01% |
| 50 mM NaCl | 8.7 mg | 50 mM |
| pH = 8 | — | pH = 8 |

Pharmaceutical Compositions

The present invention provides a pharmaceutical composition comprising a transglutaminase, e.g. a Factor XIII. This pharmaceutical composition comprises either the reconstituted solution or the dry composition of the present invention.

In one embodiment, the pharmaceutical composition is a dry composition (e.g. a freeze-dried or spray-dried composition) intended for reconstitution by the physician or the patient by addition of diluent prior to use.

The pharmaceutical compositions of the present invention containing a transglutaminase, e.g. a Factor XIII, may be administered to a patient in need of such treatment by several different routes, e.g. topically (such as by application to the skin or to a mucous membrane), by routes which bypass absorption (such as administration in an artery, in a vein or in the heart), and by routes which involve absorption (such as by administration in the skin, beneath the skin, in muscle or in the abdomen).

Administration of pharmaceutical compositions according to the present invention to patients in need thereof may be via various routes of administration, e.g. lingual, sublingual, buccal, oral, in the stomach or intestine, nasal, pulmonary (e.g. via the bronchioles and alveoli or both), epidermal, dermal, transdermal, vaginal, rectal, ocular (e.g. via the conjunctiva), urethral or parenteral.

Pharmaceutical compositions of the present invention may be administered in various dosage forms, e.g. as solutions, suspensions, emulsions, microemulsions, multiple emulsion, foams, salves, pastes, plasters, ointments, tablets, coated tablets, rinses, capsules (e.g. hard gelatin capsules or soft gelatin capsules), suppositories, rectal capsules, drops, gels, sprays, powder, aerosols, inhalants, eye drops, ophthalmic ointments, ophthalmic rinses, vaginal pessaries, vaginal rings, vaginal ointments, injection solutions, in situ transforming solutions (e.g. in situ gelling, in situ setting, in situ precipitating or in situ crystallizing), infusion solution, or as implants.

Pharmaceutical compositions of the present invention may further be compounded in, or bound or conjugated to (e.g. via covalent, hydrophobic or electrostatic interactions), a drug carrier, drug delivery system or advanced drug delivery system in order to further enhance stability of the transglutaminase, e.g. the Factor XIII, to increase bioavailability, to increase solubility, to decrease adverse effects, to achieve chronotherapy well known to those skilled in the art, and/or to increase patient compliance. Examples of carriers, drug delivery systems and advanced drug delivery systems include, but are not limited to, polymers, e.g. cellulose and derivatives thereof, other polysaccharides (e.g. dextran and derivatives thereof, starch and derivatives thereof), poly (vinyl alcohol), acrylate and methacrylate polymers, polylactic acid and polyglycolic acid and block co-polymers thereof, polyethyleneglycols, carrier proteins (e.g. albumin), gels (e.g. thermogelling systems, such as block co-polymeric systems well known to those skilled in the art), micelles, liposomes, microspheres, nanoparticulates, liquid crystals and dispersions thereof, L2 phase and dispersions thereof well known to those skilled in the art of phase behavior in lipid-water systems, polymeric micelles, multiple emulsions (self-emulsifying and self-microemulsifying), cyclodextrins and derivatives thereof, and dendrimers.

Pharmaceutical compositions of the present invention are suitable for use in the formulation of solids, semisolids, powders and solutions for pulmonary administration using, for example, a metered dose inhaler, dry powder inhaler or a nebulizer, all of which are devices well known to those skilled in the art.

Pharmaceutical compositions of the present invention are suitable for use in the formulation of controlled-release, sustained-release, protracted-release, retarded-release or slow-release drug delivery systems. Pharmaceutical compositions of the present invention are, for instance, useful in formulation of parenteral controlled-release and sustained-release systems (both systems leading to a many-fold reduction in number of administrations) of types well known to those skilled in the art, such as controlled-release and sustained-release systems for subcutaneous administration. Without limiting the scope of the present invention, examples of useful controlled-release systems and compositions are hydrogels, oleaginous gels, liquid crystals, polymeric micelles, microspheres and nanoparticles. Methods for producing controlled release systems useful for pharmaceutical compositions of the present invention include, but are not limited to, crystallization, condensation, co-crystallization, precipitation, co-precipitation, emulsification, dispersion, high-pressure homogenisation, encapsulation, spray-drying, microencapsulation, coacervation, phase separation, solvent evaporation to produce microspheres, extrusion and supercritical fluid processes. General reference is made to Handbook of Pharmaceutical Controlled Release (Wise, D. L., ed., Marcel Dekker, New York, 2000) and to Drugs and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, for example a syringe in a device of the pen type. Alternatively, parenteral administration may for instance be performed by means of an infusion pump. A further option for administration of the pharmaceutical compositions of the present invention in the form of a solution or suspension is administration as a nasal or pulmonary spray. As another option, the pharmaceutical compositions of the present invention may be adapted to transdermal administration, e.g. by needle-less injection, by application of a patch (such as an iontophoretic patch) or by transmucosal (e.g. buccal) administration.

The term "treating" in its various grammatical forms in relation to the present invention refer to curing, reversing, attenuating, alleviating, ameliorating, inhibiting, minimizing, suppressing, or halting (1) the deleterious effects of a disorder, (2) disorder progression, or (3) disorder causative agent.

In the context of the present invention, an "effective amount" of a pharmaceutical composition is defined as the amount of a pharmaceutical composition, e.g. Factor XIII, that is sufficient for preventing, curing, reversing, attenuating, alleviating, ameliorating, inhibiting, minimizing, suppressing, or halting (1) the deleterious effects of a disorder, (2) disorder progression, or (3) disorder causative agent, alone or in combination with other administered therapeutic agents.

It has been described that Factor XIII may be used for treating or preventing bleeding episodes, in patients having a congenital Factor XIII deficiency as well as in patients not having a congenital Factor XIII deficiency, see for instance U.S. Pat. No. 5,114,916, U.S. Pat. No. 5,607,917, WO 2002038167, WO 2002036155, WO 200267981, and WO 200267980.

The present invention provides a method for treating or preventing bleeding episodes, which method comprises administration of an effective amount of the pharmaceutical composition of the present invention, comprising a FXIII, to a subject in need thereof. In a further embodiment, the present invention relates to a method for reducing clotting time in a subject, which method comprises administration of the pharmaceutical composition of the present invention to a subject in need thereof. In a further embodiment, the present invention relates to a method for prolonging the clot lysis time in mammalian plasma, which method comprises administration of the pharmaceutical composition of the present invention to a subject in need thereof. In a further embodiment, the present invention relates to a method for increasing clot strength in mammalian plasma, which method comprises administration of an effective amount of the pharmaceutical composition of the present invention to a subject in need thereof. In a further embodiment, the present invention relates to a method for enhancing fibrin clot formation in mammalian plasma, which method comprises administration of an effective amount of the pharmaceutical composition of the present invention to a subject in need thereof. In a further embodiment, the present invention relates to a method for prevention of intraventricular hemorrhage in premature infants, which method comprises administration of an effective amount of the pharmaceutical composition of the present invention to a subject in need thereof. In a further embodiment, the present invention relates to a method for reducing surgery-related blood loss in a subject during or after surgery, which method comprises administration of an effective amount of the pharmaceutical composition of the present invention to a subject in need thereof. In a further embodiment, the present invention relates to a method for treating hemophilia A, which method comprises administration of an effective amount of the pharmaceutical composition of the present invention to a subject in need thereof. In a further embodiment, the present invention relates to a method for treating hemophilia B, which method comprises administration of an effective amount of the pharmaceutical composition of the present invention to a subject in need thereof. In a further embodiment, the present invention relates to a method for treating platelet disorders, which method comprises administration of an effective amount of the pharmaceutical composition of the present invention to a subject in need thereof. In a further embodiment, the present invention relates to a method for treating von Willebrand's disease, which method comprises administration of an effective amount of the pharmaceutical composition of the present invention to a subject in need thereof.

The pharmaceutical composition of the present invention, when comprising FXIII, is further useful in systemic or local application to treat conditions including bone or would healing, ulcerative colitis, scleroderma, Scholein Henoch purpura, subarchnoidal hemorrhage, intraventricular bleeding, and bleedings for unknown reasons.

In a further embodiment of these methods, the pharmaceutical composition of the present invention, e.g. comprising Factor XIII, is administered in combination with an effective amount of a factor VIIa as described in WO 200185198.

In some embodiments, the pharmaceutical composition of the present invention is the sole active agent administered to the subject for the indicated treatment.

In one embodiment, the subject to be treated is a human; in one embodiment, the subject has an impaired thrombin production; in one embodiment, the subject has a lowered plasma concentration of fibrinogen (e.g., in the case of a multi-transfused subject).

The present invention, thus generally described, will be understood more readily by reference to the following examples, which are provided by way of illustration and are not intended to be limiting of the present invention.

EXAMPLES

To develop the compositions of the present invention, various compositions were studied, together with their effects on the subsequent stability of the compositions during storage.

Example 1 Lyophilization and Reconstitution of Factor XIII

Freeze-drying experiments were carried out in commercially available lyophilizers. Solutions of recombinant Factor XIII, prepared by expression in yeast cells, together with additional components were dried in accordance with a suitable freeze-drying program. The lyophilisates were then reconstituted using distilled water.

Example 2: Stability of Dry Factor XIII Compositions

A series of dry rFXIII compositions were prepared by lyophilization, according to Example 1, and placed on a stability study where purity was measured by AIE-HPLC and aggregates was measured by SEC-HPLC. This study investigated three levels of NaCl included in the aqueous filling solution, 0 mM, 12.5 mM and 25 mM NaCl and four levels of sucrose as given in Table 3 and 4.

TABLE 3

Compositions studied in the presence and absence of NaCl

| | DP filling solution used for CD indication | Compositions studied | | | |
|---|---|---|---|---|---|
| | | Ratio 1 | Ratio 2 | Ratio 3 | Ratio 4 |
| rFXIII, mg/ml | 2.5 | 5.0 | 5.0 | 5.0 | 5.0 |
| Sucrose, mg/ml | 42.5 | 80 | 40 | 20 | 0 |
| Histidine, mM | 20 | 20 | 20 | 20 | 20 |
| Polysorbate 20 | 0.01% | 0.01% | 0.01% | 0.01% | 0.01% |
| Sucrose-to-protein ratio | 17 | 16 | 8 | 4 | 0 |

TABLE 4

Content of Sucrose and NaCl

| Exp Name | Sucrose | NaCl |
|---|---|---|
| N1 | 0 | 0 |
| N2 | 20 | 0 |
| N3 | 40 | 0 |
| N4 | 80 | 0 |
| N5 | 0 | 25 |
| N6 | 20 | 25 |
| N7 | 40 | 25 |
| N8 | 80 | 25 |
| N9 | 0 | 12.5 |
| N10 | 0 | 12.5 |
| N11 | 0 | 12.5 |
| N12 | 0 | 12.5 |

TABLE 5

Table of results

| No | AIE-purity 0 | AIE-purity 1M40 | SEC % aggr 0 | SEC % aggr M40 | SEC % aggr M40 | AIE-purity 2M40 | SEC % aggr 3M40 | SEC % aggr 3M25 |
|---|---|---|---|---|---|---|---|---|
| N1 | 3.87 | 3.95 | 0.2 | 0.6 | 0.9 | 61 | 1 | 0.5 |
| N2 | 74.75 | 65.87 | 0.05 | 0.1 | 0.1 | 61 | 0.1 | 0.1 |
| N3 | 74.48 | 66.47 | 0.05 | 0.1 | 0.1 | 64.4 | 0.1 | 0.1 |
| N4 | 74.75 | 69.74 | 0.1 | 0.1 | 0.1 | 66.2 | 0.1 | 0.1 |
| N5 | 73.39 | 71.67 | 4.1 | 1.6 | 1.8 | 66.9 | 2.3 | 1.9 |
| N6 | 75.11 | 72.42 | 0.1 | 0.1 | 0.1 | 68.5 | 0.1 | 0.1 |
| N7 | 75.13 | 72.32 | 0.1 | 0.1 | 0.1 | 68.9 | 0.1 | 0.1 |
| N8 | 74.05 | 72.61 | 0.1 | 0.1 | 0.1 | 69.5 | 0.1 | 0.1 |
| N9 | 72.63 | 69.14 | 1.8 | 1.3 | 1.5 | 65.8 | 1.6 | 1.2 |
| N10 | 72.33 | 69.57 | 1.7 | 1.4 | 1.4 | 66.6 | 1.5 | 1.2 |
| N11 | 72.79 | 69.71 | 1.7 | 1.2 | 1.5 | 65.7 | 1.7 | 1.2 |
| N12 | 72.74 | 69.05 | 1.7 | 1.4 | 1.5 | 66.8 | 1.3 | 1.2 |

Figure 1:
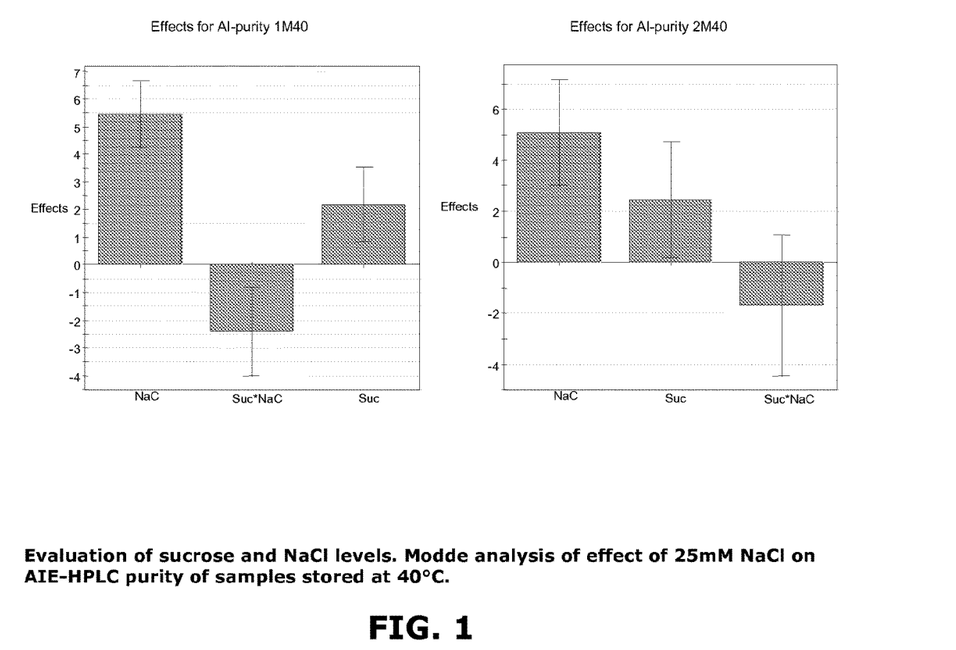
FIG. 1: Evaluation of sucrose and NaCl levels. Mode analysis of effect of 25 mM NaCl on AIE-HPLC purity of samples stored at 40° C.

The results presented in Table 5 and FIG. 1 demonstrates that there is a statistically significant relationship between NaCl and AIE-HPLC purity for samples stored at 40° C. There is not an effect on the initial purity of the samples. Therefore, it is concluded that NaCl acts specifically on the dry state, i.e. the dry composition, thereby significantly improving the storage stability of the dry rFXIII compositions.

Example 3: Full Factorial Study

The purpose of the study was to perform a preliminary screening experiment on lyophilized formulations of rFXIII to investigate the effects of histidine and sodium chloride, on the formation of rFXIIIa° upon lyophilization. A full factorial design of experiment was utilized to evaluate histidine concentration over the range 20-60 mM and NaCl concentration over the range 0-50 mM in dry rFXIII compositions.

TABLE 6

Experimental Factors

| No. | NaCl | Histidine |
|---|---|---|
| N1 | 0 | 20 |
| N2 | 25 | 20 |
| N3 | 50 | 20 |
| N4 | 0 | 40 |
| N5 | 25 | 40 |
| N6 | 50 | 40 |
| N7 | 0 | 60 |
| N8 | 25 | 60 |
| N9 | 50 | 60 |
| N10 | 25 | 40 |
| N11 | 25 | 40 |
| N12 | 25 | 40 |

TABLE 7

Table of results

| No | % act initial | % act 2M25 | AIE purity 2M25 | SEC 2M25 | % act 1M40 | % act 4M25 |
|---|---|---|---|---|---|---|
| N1 | 0.4 | 1.1 | 67.4 | 0.1 | 2.6 | 1.8 |
| N2 | 0.4 | 0.7 | 70.3 | 0.1 | 1.6 | 1.2 |
| N3 | 0.4 | 0.7 | 71 | 0.1 | 1.5 | 1.1 |
| N4 | 0.4 | 1.1 | 67.8 | 0.1 | 2.3 | 2 |
| N5 | 0.5 | 0.8 | 70.3 | 0.2 | 1.8 | 1.2 |
| N6 | 0.4 | 0.7 | 71 | 0.2 | 1.3 | 1 |
| N7 | 0.4 | 1.2 | 68.4 | 0.1 | 2.3 | 2 |
| N8 | 0.4 | 0.9 | 70.3 | 0.2 | 1.6 | 1.3 |
| N9 | 0.5 | 0.8 | 70.8 | 0.2 | 1.3 | 1 |
| N10 | 0.6 | 0.9 | 70.5 | 0.1 | 1.7 | 1.2 |
| N11 | 0.4 | 1 | 70.2 | 0.1 | 1.7 | 1.3 |
| N12 | 0.4 | 0.8 | 70.2 | 0.5 | 1.5 | 1.1 |

| No | AIE purity 4M25 | SEC 4M25 | % act 6M25 | SEC 6M25 | AIE purity 6M25 | AIE purity initial |
|---|---|---|---|---|---|---|
| N1 | 65.1 | 0.1 | 2.2 | 0.1 | 63.5 | 72.1 |
| N2 | 69.2 | 0.1 | 1.4 | 0.1 | 68 | 72.4 |
| N3 | 70.2 | 0.1 | 1.1 | 0.1 | 69.5 | 72.3 |
| N4 | 66 | 0.1 | 2.2 | 0.1 | 64.6 | 71.8 |
| N5 | 69 | 0.2 | 1.4 | 0.2 | 68.3 | 72.1 |
| N6 | 70 | 0.2 | 1.1 | | | 72.2 |
| N7 | 67.1 | 0.1 | 2 | 0.1 | 65.3 | 71.9 |
| N8 | 69.8 | 0.2 | 1.5 | 0.2 | 68.6 | 72.2 |
| N9 | 70 | 0.2 | 1.3 | 0.2 | 69.6 | 72.3 |
| N10 | 69.5 | 0.1 | 1.3 | 0.1 | 68.9 | 72.3 |
| N11 | 69.6 | 0.1 | 1.4 | 0.1 | 69 | 72.3 |
| N12 | 69.2 | 0.1 | 1.4 | 0.1 | 68.9 | 72.3 |

Figure 2:
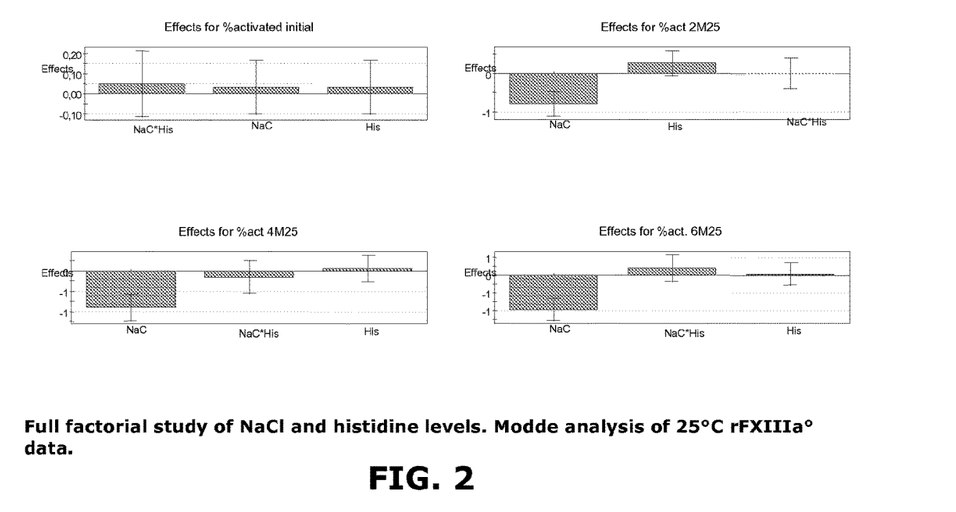
FIG. 2: Full factorial study of NaCl and histidine levels. Mode analysis of 25° C. rFXIIIa° data.
Figure 3:
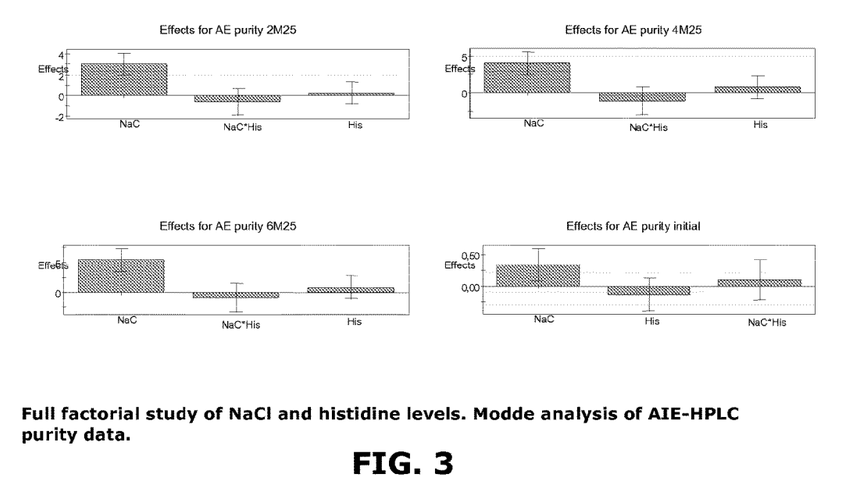
FIG. 3: Full factorial study of NaCl and histidine levels. Mode analysis of AIE-HPLC purity data.

The results presented in Table 7 and FIGS. 2 and 3 demonstrate that the inclusion of NaCl has a significant stabilizing effect on purity and on the formation of rFXIIIa° for samples stored at 40° C. and 25° C. for 1 and 2 months, respectively. The inclusion of NaCl has no significant effect on samples at the initial time-point. The NaCl and histidine levels studied herein have no significant effects on aggregate levels by SE-HPLC after 2 months at 25° C. This study shows that including NaCl in the dry rFXIII composition significantly improves the storage stability of the composition with respect to % purity and % rFXIIIa°.

Example 4: Reconstitution Study

This experiment was performed to verify that the stabilizing effect of NaCl is specific to the dry state, i.e. the dry composition. In this experiment a vial of lyophilized rFXIII composition was reconstituted with water then divided into two equal volumes to which one NaCl was added. The solutions were stored at room temperature for 24 hours then analysed for rFXIIIa°. Three concentrations of NaCl were evaluated. The experimental design is depicted in Table 8.

TABLE 8

Experimental design - Effect of NaCl on rFXIIIa° formation in solution 12 mL vial containing rFXIII drug product powder

| Vial #1. Reconstitute with 2.5 mL of water | Vial #2. Reconstitute with 2.5 mL of water | Vial #3. Reconstitute with 2.5 mL of water |
|---|---|---|
| 0 mM NaCl 25 mM NaCl Store solution at room temperature for 24 hours then analyze | 0 mM NaCl 50 mM NaCl Store solution at room temperature for 24 hours then analyze | 0 mM NaCl 75 mM NaCl Store solution at room temperature for 24 hours then analyze |

TABLE 9

Potency results from NaCl reconstitution study

| Sample ID | NaCl Concentration (mM) | Total rFXIII (IU/ml) | rFXIIIa (IU/ml) | % rFXIIIa° (Analysed 24 hours after reconstitution) |
|---|---|---|---|---|
| 1a | 0 | 957 | 5.0 | 0.5 |
| 1b | 25 | 854 | 5.6 | 0.7 |
| 2a | 0 | 889 | 4.4 | 0.5 |
| 2b | 50 | 887 | 5.1 | 0.6 |
| 3a | 0 | 990 | 4.1 | 0.4 |
| 3b | 75 | 837 | 5.7 | 0.7 |

The results presented in Table 9 show that the samples containing NaCl have slightly higher rFXIIIa° values after 24 hours than the respective comparator solutions containing no NaCl. These results demonstrate that, over the concentration range 25-75 mM, NaCl in aqueous composition does not have a stabilizing effect with respect to the formation of rFXIIIa°. It is concluded that the stabilizing effects of NaCl in lyophilized rFXIII composition, demonstrated by the data of Examples above, is specific to the dry state (dry composition). This effect is surprising and heretofore unknown.

Assays

Assay (I): Method of Measuring FXIIIa°

To study the effects of lyophilization, on the amount of FXIIIa°, purified recombinant Factor XIII may be analysed by an enzymatic FXIII activity assay, where the FXIIIa° activity is measured by comparing the activity of an aliquot of a sample without initial thrombin activation, with that of another aliquot of the same sample added thrombin. % FXIIIa° is calculated as 100*[activity of sample without thrombin]/[activity of sample with thrombin.

Assay (II): Method of Measuring FXIII Purity

To study the effects of lyophilization, on the purity of FXIII, purified recombinant FXIII may be analysed by anion-exchange high performance liquid chromatography (AIE-HPLC).

Assay (III): Methods of Measuring FXIII Activity

Methods of measuring FXIII cross-linking activity are well known in the art. FXIII activity may be measured using commercially available kits, such as the Berichrom FXIIIR test kit.

Assay (IV): Method of Measuring Moisture Content

To study the moisture content of the dry transglutaminase, e.g. FXIII, composition, Karl Fischer Titration may be used.

Preferred Features of the Invention:

1. Dry transglutaminase composition, said composition is obtainable by lyophilizing or spray-drying an aqueous composition comprising a transglutaminase, a salt and at least one further component selected from the group consisting of a sugar, an amino acid, and a buffer, wherein the concentration of the salt in the aqueous composition is in the range from 5 to 100 mM.

2. Composition according to clause 1, wherein the transglutaminase is a Factor XIII compound.

3. Composition according to clause 2, wherein the Factor XIII compound is a human Factor XIII.

4. Composition according to any one of clauses 2-3, wherein the Factor XIII compound is a recombinant Factor XIII.

5. Composition according to any one of clauses 2-4, wherein the Factor XIII compound is a dimer of A subunits.

6. Composition according to clause 2, wherein the Factor XIII compound is selected from the group consisting of Factor XIII, and biologically active fragments, derivatives, and variants thereof that retain at least part of the characteristic cross-linking activity of the wild-type Factor XIII.

7. Composition according to any one of clauses 1-6, wherein the concentration of said Factor XIII compound is in the range from 1 to about 100 mg/ml.

8. Composition according to any one of clauses 1-7, wherein the salt is a monovalent salt.

9. Composition according to clause 8, wherein the monovalent salt is a sodium chloride salt.

10. Composition according to any one of clauses 1-9, wherein the concentration of said salt in the aqueous composition is in the range from 10 to 75 mM.

11. Composition according to clause 10, wherein the concentration of said salt in the aqueous composition is in the range from 20 to 60 mM.

12. Composition according to any one of clauses 1-11, wherein the aqueous composition comprises a sugar and wherein said sugar is a sugar or sugar alcohol selected from the group of sucrose, mannitol, trehalose, lactose, maltose, sorbitol, raffinose, dextrin, cyclodextrin, and the derivatives, homologs, and mixtures thereof.

13. Composition according to clause 12, wherein the concentration of said sugar and sugar alcohol is between 0.1% and 8.5% (w/w).

14. Composition according to any one of clauses 1-13, wherein the aqueous composition comprises an amino acid and wherein said amino acid is selected from the group of glycine, histidine and arginine.

15. Composition according to any one of clauses 1-14, wherein the aqueous composition comprises a buffer and wherein said buffer is selected from the group of citrate, histidine sodium phosphate, succinate, and TRIS.

16. Composition according to any one of clauses 1-15, wherein the aqueous composition furthermore comprises one or more further components selected from the group consisting of a non-ionic surfactant, a reducing agent, a chelating agent, an antioxidant, a preservative, a wetting agent, an emulsifier, a bulking agent, a tonicity modifier, and a zwitterionic substance.

17. Composition according to any one of clauses 1-16, wherein the composition is in a powder form.

18. Composition according to any one of clauses 1-17, wherein the dry composition contains less than 3% moisture.

19. Composition according to clause 18, wherein the dry composition contains less than 1% moisture.

20. Method of preparing a dry composition according to any one of clauses 1-19 by drying an aqueous composition comprising a transglutaminase, a salt and at least one further component selected from the group consisting of a sugar, an amino acid, and a buffer, wherein the concentration of the salt in the aqueous composition is in the range from 5 to 100 mM.

21. Method according to clause 20, wherein the drying of the aqueous composition is preformed by lyophilization or spray-drying.

22. Method according to any one of clauses 20-21, wherein the method is used to produce a Factor XIII composition which after reconstitution comprises no more than 1% non-proteolytically activated Factor XIII.
23. Reconstituted solution comprising a transglutaminase, wherein said solution is prepared by reconstituting the dry composition according to any one of clauses 1-19 in a diluent.
24. Solution according to clause 23, wherein said diluent is distilled water.
25. Solution according to clause 23, wherein said diluent is a diluent comprising one or more further components selected from the group consisting of a salt, a sugar, an amino acid, a buffer, a non-ionic surfactant, a reducing agent, a chelating agent, an antioxidant, a preservative, a wetting agent, an emulsifier, a bulking agent, a tonicity modifier, an oleaginous vehicle, a protein and a zwitterionic substance.
26. Solution according to any one of clauses 23-25, wherein the transglutaminase is a Factor XIII compound.
27. Solution according to clause 26, wherein no more than 1% of said Factor XIII compound is non-proteolytically activated Factor XIII.
28. Solution according to clause 27, wherein no more than 0.5% of said Factor XIII compound is non-proteolytically activated Factor XIII.
29. Pharmaceutical composition comprising the solution according to any one of clauses 23-28 or the dry composition according to any one of clauses 1-19.
30. Pharmaceutical composition according to clause 29 for reducing blood loss.
31. Pharmaceutical composition according to clause 29 for the prevention of intraventricular hemorrhage in premature infants.
32. Pharmaceutical composition according to clause 29 for reducing surgery-related blood loss in a patient during or after surgery.
33. Pharmaceutical composition according to clause 29 for treating hemophilia A.
34. Pharmaceutical composition according to clause 29 for treating hemophilia B.
35. Pharmaceutical composition according to clause 29 for treating platelet disorders.
36. Pharmaceutical composition according to clause 29 for treating von Willebrand's disease.
37. Method of treating or preventing bleeding episodes, comprising administering an effective amount of the pharmaceutical composition according to clause 29 to a subject in need thereof.
38. Method for reducing clotting time in a subject, comprising administering the pharmaceutical composition according to clause 29 to a subject in need thereof.
39. Method for reducing clotting time in a subject, comprising administering the pharmaceutical composition according to clause 29 to a subject in need thereof.
40. Method for increasing clot strength, comprising administering the pharmaceutical composition according to clause 29 to a subject in need thereof.
41. Method for enhancing fibrin clot formation, comprising administering the pharmaceutical composition according to clause 29 to a subject in need thereof.
42. Method for prevention of intraventricular hemorrhage in premature infants, comprising administering an effective amount of the pharmaceutical composition according to clause 29 to a subject in need thereof.
43. Method for reducing surgery-related blood loss in a subject during or after surgery, comprising administering an effective amount of the pharmaceutical composition according to clause 29 to a subject in need thereof.
44. Method for treating hemophilia A, comprising administering an effective amount of the pharmaceutical composition according to clause 29 to a subject in need thereof.
45. Method for treating hemophilia B, comprising administering an effective amount of the pharmaceutical composition according to clause 29 to a subject in need thereof.
46. Method for treating platelet disorders, comprising administering an effective amount of the pharmaceutical composition according to clause 29 to a subject in need thereof.
47. Method for treating von Willebrand's disease, comprising administering an effective amount of the pharmaceutical composition according to clause 29 to a subject in need thereof.
48. Method for stabilizing a transglutaminase composition during storage in dried form, so that the level of non-proteolytically activated transglutaminase constitutes no more than 1% of the total transglutaminase content measured directly after reconstitution, wherein the stabilizing effect is provided by drying an aqueous composition comprising a transglutaminase, a salt and at least one further component selected from the group consisting of a sugar, an amino acid, and a buffer, wherein the concentration of the salt in the aqueous composition is in the range from 5 to 100 mM.
49. Method according to clause 48, wherein the transglutaminase composition is a Factor XIII composition.

The invention claimed is:
1. A dry Factor XIII composition comprising (a) a Factor XIII compound, (b) monovalent salt, and (c) at least one further component selected from the group consisting of a sugar and an amino acid; wherein the Factor XIII compound is selected from the group consisting of wild-type Factor XIII and a dimer of A subunits of Factor XIII; wherein the monovalent salt is in an amount corresponding to a concentration of 20-60 mM when the composition is reconstituted with 3 ml of water; and wherein the composition achieves a level of non-proteolytically activated Factor XIII that constitutes no more than 1% of the total Factor XIII content when measured after reconstitution after being stored at 25° C. for 2 months.
2. The composition according to claim 1, wherein the Factor XIII compound is a dimer of A subunits of human Factor XIII.
3. The composition according to claim 1, wherein the composition is in a powder form.
4. A method of preparing a dry Factor XIII composition, comprising drying an aqueous composition comprising (a) a Factor XIII compound, (b) a monovalent salt, and (c) at least one further component selected from the group consisting of a sugar, an amino acid, a buffer, and a non-ionic surfactant; wherein the Factor XIII compound is selected from the group consisting of wild-type Factor XIII and a dimer of A subunits of Factor XIII; wherein the monovalent salt is present in a concentration in the aqueous composition in a range from 20-60 mM; and wherein the composition achieves a level of non-proteolytically activated Factor XIII that constitutes no more than 1% of the total Factor XIII content when measured after reconstitution after being stored at 25° C. for 2 months, respectively.
5. A pharmaceutical composition comprising the dry Factor XIII composition according to claim 1.
6. The composition according to claim 1, wherein the monovalent salt is selected from the group consisting of sodium chloride, potassium chloride, sodium acetate, sodium sulphate, sodium gluconate, and mixtures thereof.

7. The composition according to claim 6, wherein the monovalent salt is sodium chloride.

8. The composition according to claim 1, wherein the sugar is selected from the group consisting of sucrose, mannitol, trehalose, lactose, maltose, sorbitol, raffinose, dextrins, cyclodextrins, and mixtures thereof.

9. The composition according to claim 8, wherein the sugar is sucrose.

10. The composition according to claim 1, wherein the amino acid is selected from the group consisting of glycine, histidine, arginine, glutamic acid, methionine, threonine, lysine, alanine, isoleucine, cysteine, and mixtures thereof.

11. The composition according to claim 10, wherein the amino acid is histidine.

12. A dry Factor XIII composition, comprising (a) a recombinant human Factor XIII compound that is a dimer of A subunits of Factor XIII, (b) sodium chloride, (c) sucrose, (d) histidine, and (e) Tween 20; wherein the sodium chloride is in an amount corresponding to a concentration of 25-50 mM when the composition is reconstituted with 3 ml of water; and wherein the composition achieves a level of non-proteolytically activated Factor XIII that constitutes no more than 1% of the total Factor XIII content when measured after reconstitution after being stored at 25° C. for 2 months.

13. The method according to claim 4, wherein the drying is performed by lyophilizing the aqueous composition.

14. The method according to claim 4, wherein the monovalent salt is selected from the group consisting of sodium chloride, potassium chloride, sodium acetate, sodium sulphate, sodium gluconate, and mixtures thereof.

15. The method according to claim 14, wherein the monovalent salt is sodium chloride.

16. The method according to claim 15, wherein the sodium chloride is present in a concentration in the aqueous composition in a range from 25-50 mM.

17. The method according to claim 4, wherein the sugar is selected from the group consisting of sucrose, mannitol, trehalose, lactose, maltose, sorbitol, raffinose, dextrins, cyclodextrins, and mixtures thereof.

18. The method according to claim 17, wherein the sugar is sucrose.

19. The method according to claim 4, wherein the amino acid is selected from the group consisting of glycine, histidine, arginine, glutamic acid, methionine, threonine, lysine, alanine, isoleucine, cysteine, and mixtures thereof.

20. The method according to claim 19, wherein the amino acid is histidine.

21. The method according to claim 4, wherein the buffer is selected from the group consisting of acetate buffers, carbonate buffers, citrate buffers, glyclyglycine buffers, histidine buffers, glycine buffers, lysine buffers, arginine buffers, phosphate buffers, TRIS buffers, bicine buffers, tricine buffers, malate buffers, succinate buffers, maleate buffers, fumarate buffers, tartrate buffers, aspartate buffers, and mixtures thereof.

22. The method according to claim 21, wherein the buffer is a TRIS buffer.

23. The method according to claim 4, wherein the non-ionic surfactant is selected from the group consisting of Tween 80, Tween 20, PEG, acetyl alcohol, PVP, PVA, lanolin alcohol, sorbitan monooleate, poloxamers, and polyoxyethylene alkyl ethers.

24. The method according to claim 23, wherein the non-ionic surfactant is Tween 20.

25. A method of preparing a dry Factor XIII composition, comprising drying an aqueous composition comprising (a) a recombinant human Factor XIII compound that is a dimer of A subunits of Factor XIII, (b) sodium chloride in a concentration of 25-50 mM, (c) sucrose, (d) histidine, and (e) Tween 20; wherein the composition achieves a level of non-proteolytically activated Factor XIII that constitutes no more than 1% of the total Factor XIII content when measured after reconstitution after being stored at 25° C. for 2 months.

26. The composition according to claim 12, wherein the Factor XIII is present in an amount of 15 mg; wherein the sodium chloride is present in an amount of 8.7 mg; wherein the histidine is presented in amount of 9.3 mg; and wherein the Tween 20 is presented in an amount of 0.3 mg.

* * * * *